United States Patent [19]

Gudov et al.

[11] Patent Number: 5,067,952
[45] Date of Patent: Nov. 26, 1991

[54] METHOD AND APPARATUS FOR TREATING MALIGNANT TUMORS BY LOCAL HYPERPYREXIA

[76] Inventors: Vasily F. Gudov, ulitsa Kachalova, 16, kv. 1, Moscow; Nikolai E. Yakhontov, Ulitsa Osharskaya, 52a, kv. 2, Gorky; Vladimir P. Kharchenko, ulitsa akademika Piljugina, 8, kv. 484, Moscow; Boris K. Dolotov, Ulitsa Proletarskaya, 5, kv. 301, Gorky; Evgeny L. Belousov, ulitsa Semashko, 2, kv. 49, Gorky; Valery B. Vinitsky, Leningradskoe shosse, 78, kv. 20, Moscow; Alexandr M. Kozlov, ulitsa Lesnaya, 10, kv. 162, Moskovskaya oblast, Reutov; Mikail G. Akhalaya, ulitsa Lenina, 24, kv. 7, Sukhumi; Alexandr D. Koveshinikov, ulitsa Kirovogradskaya, 44, korpus 8, kv. 160, Moscow; Valery F. Pugachev, prospekt Tsiolkovskogo, 30, kv. 43, Gorkovskaya oblast, Dzerzhinsk, all of U.S.S.R.

[21] Appl. No.: 503,529

[22] Filed: Apr. 2, 1990

[51] Int. Cl.⁵ .................. A61B 17/36; A61N 2/10
[52] U.S. Cl. .................. 606/28; 600/10; 600/12
[58] Field of Search .......... 606/28; 600/12, 13, 600/9, 10

[56] References Cited

U.S. PATENT DOCUMENTS

| 4,346,715 | 8/1982 | Gammell | 128/422 |
|---|---|---|---|
| 4,545,368 | 10/1985 | Rand et al. | 600/12 |
| 4,574,782 | 3/1986 | Borrelli et al. | 600/10 |
| 4,590,922 | 5/1986 | Gordon | 600/10 |
| 4,690,130 | 9/1987 | Mirell | 600/10 |
| 4,735,796 | 5/1988 | Gordon | 600/12 |
| 4,763,671 | 8/1988 | Goffmet | 128/804 |
| 4,815,446 | 3/1989 | McIntosh | 600/3 |
| 4,829,984 | 5/1989 | Gordon | 600/12 |
| 4,922,902 | 5/1990 | Wuchinich et al. | 604/22 |

OTHER PUBLICATIONS

Application of Hyperpyrexia and Hyperglycemia in Treating Malignant Tumors—Moscow, Meditsina Publishing House (1980).

Primary Examiner—Kyle L. Howell
Assistant Examiner—Krista M. Pfaffle
Attorney, Agent, or Firm—Burgess, Ryan & Wayne

[57] ABSTRACT

A method is provided wherein a suspension containing ferromagnetic particles is introduced into a body, and the particles are caused to move towards a tumor and are retained there by a magnetic field. The area of the tumor is exposed to an electromagnetic field to carry out hyperpyrexia of the tumor to a temperature sufficient to kill cancer cells. The contents of the tumor are removed. The condition of a patient's body is monitored during the treatment by determining activity of neutrophils and macrophages. An apparatus is also provided for carrying out the method and comprises an electromagnetic radiation source with emitters, temperature pickups, and a temperature setter connected to inputs of a comparator, a temperature control unit for controlling hyperpyrexia temperature connected to an output of the comparator and forming a signal fed to a control input of the source of radiation. The apparatus is also provided with a magnetic retainer for retaining ferromagnetic particles within the boundaries of a tumor, aa device for removing contents of a tumor, and a device for transferring ferromagnetic particles towards a tumor.

8 Claims, 6 Drawing Sheets

METHOD AND APPARATUS FOR TREATING MALIGNANT TUMORS BY LOCAL HYPERPYREXIA

BACKGROUND OF THE INVENTION

1) Field of the Invention

The invention relates to a method and apparatus for treating malignant tumors by local hyperpyrexia.

The invention is aimed at treating malignant tumors in any part of a human body with single or multiple neoplasms and their metastases.

2) Description of the Related Art

It is known from Soviet and foreign literature that cancer cells die at 43.5° C. within 90 minutes and that normal cells survive at 45.5° C. after the same exposure.

As far back as five thousand years ago general hyperpyrexia of a human body at 44° C. was practiced in China for periods as long as two hours so as to treat any disease. However, about 95% of patients could not withstand high temperature and died.

Also known in the art is a method for treating malignant tumors by local hyperpyrexia at a temperature which is high enough to kill cancer cells by acting with an electromagnetic field (cf. N. N. Alexandrov et al. Primenenie Gipertermii i Giperglikemii pri Lechenii Zlokachestvennykh Opukholei/Application of Hyperpyrexia and Hyperglycemia in Treating Malignant Tumors/, Moscow, "Moditsina Publishing House", 1980, pp. 91-95).

When this prior art method is used for the treatment, a portion of a patient's body is exposed, in a zone where a neoplasm is located, to an alternating electromagnetic radiation in a microwave band to achieve a local hyperpyrexia of the neoplasm to 43.5° C. for about two hours. This method is, however, only applicable for treating surface malignant tumors such as tumors on the skin surface, in subcutaneous fat, and in a muscle at a maximum depth of 2 cm since the use of SHF oscillations (2450 MHz) allows tissues to be heated to 43.5° C. to a depth of 1.5 to 2.0 cm only. Temperature than gradually decreases to 41°; 40°; 39°; and 38° C. Meanwhile it is known that growth of cancer tumors is stimulated at 38° to 40° C. When a high-frequency field (13.56 MHz) is used, a non-uniform heating of tissues takes place, and the subcutaneous fat layer is overheated 17 times greater than the muscular layer which results in burns when attempts are made to carry out treatment of neoplasms of internal organs using the conventional method.

Also known in the art is an apparatus for treating malignant tumors by local hyperpyrexia using an electromagnetic field. The known apparatus comprises a common base supporting a power supply, a controlled source of electromagnetic radiation connected to its output and having an output to which are connected emitters coupled to the source by means of flexible holders, temperature pickups connected, via an amplifier unit, to a first input of a comparison circuit, a temperature setter connected to a second input of the comparison circuit, and a temperature control unit having an input connected to an output of the comparison circuit and an output connected to a control input of the source of electromagnetic radiation (cf. N. N. Alexandrov et al. "Primenenie Gipertermii i Giperglikemii pri Lechenii Zlokachestvennykh Opukholei" "Application of Hyperpyrexia and Hyperglycemia in Treating Malignant Tumors"/, 1980, "Meditsina Publishing House", Moscow, pp. 96-140).

This prior art apparatus allows a temperature set up by the setter to be automatically maintained in the zone of a neoplasm. However, this apparatus can only be used for treating surface neoplasms in view of the above considerations in respect of the known treatment method.

SUMMARY OF THE INVENTION

It is one object of the invention to enhance efficiency of treatment of malignant tumors.

Another object of the invention is to lower traumatism in carrying out a safe treatment of malignant tumors in substantially any part of a human body.

A further object of the invention is to provide a reliable and handy apparatus for treating malignant tumors in any part of a human body by local hyperpyrexia.

These objects are accomplished by a method for treating malignant tumors by local hyperpyrexia at a temperature which is high enough for killing cancer cells by using an electromagnetic field. According to the invention, a suspension containing ferromagnetic particles of a size ranging from $5 \times 10^{-3}$ to $30 \times 10^3$ μm is introduced into a patient's body in an amount of 0.01 to 0.5 g per each cu. cm of a neoplasm before the exposure to the electromagnetic field, movement of ferromagnetic particles within the body is X-ray controlled and, when the ferromagnetic particles reach the boundaries of the neoplasm, the patient's body is simultaneously exposed to electromagnetic field for carrying out hyperpyrexia and to a magnetic field to retain the ferromagnetic particles within the limits of the neoplasm, the condition of the patient's body being monitored during the treatment by measuring activity of neutrophils and macrophages.

It is preferred, to carry out the mechanical disintegration, that the neoplasm be exposed to ultrasonic oscillations at a frequency from 22 to 100 kHz with an intensity of 4 to 100W per sq. cm of the neoplasm surface area after the hyperpyrexia for a period of 0.1 to 5 minutes, with subsequent removal of the neoplasm contents.

It is preferred that the monitoring of condition of the body during the treatment be carried out in the following manner. Activity of neutrophils and macrophages should be determined before the introduction of suspension with ferromagnetic particles into the patient's body and, if the activity is below 100 bacteria per 100 neutrophils, tafcyn should be administered intravenously in a dose of 0.01 to 20 mg per 1 kg of a patient weight. The suspension with ferromagnetic particles is then introduced, and hyperpyrexia is carried out using the electromagnetic field. The activity of neutrophils and macrophages is again determined and, if the activity is lower than 100 bacteria per 100 neutrophils, the administration of tafcyn, also known as tuftsin; however, hereinafter referred to as tafcyn, introduction of suspension with ferro-magnetic particles and hyperpyrexia are repeated and, if activity is higher than 100 bacteria per 100 neutrophils, the neoplasm is irradiated with ultrasonic oscillations. After the removal of contents of the neoplasm, the activity of neutrophils and macrophages is again determined and, if the activity is in excess of 100, the treatment is stopped. If the activity is below 100 bacteria per 100 neutrophils, the treatment should be completely repeated.

In case neoplasms are treated in a mascular tissue, it is preferred that a suspension containing ferromagnetic particles of a size from 1 μm to 30,000 μm be used, the suspension being introduced directly into the neoplasm.

If a tumor is very thick, or if it is located deep under the surface, it is preferred, prior to the exposure to electromagnetic field, that metal needle electrodes be introduced into the neoplasm which should be uniformly distributed over the entire neoplasm area and deep through the whole thickness of the neoplasm.

In case of treatment of neoplasms of internal organs and metastases, a suspension is preferably used which contains ferromagnetic particles of a size from $5 \times 10^{-3}$ to 1 μm, the suspension being introduced intravascularly so as to transfer the ferromagnetic particles to a neoplasm under the action of magnetic field.

In case of multiple metastases and malignant tumors in various internal organs and soft tissues, it is preferred that the suspension be introduced into a vascular bed and also locally, into the largest neoplasms, the electromagnetic field being applied to the whole body with the exception of the head, the general hyperpyrexia of the body being carried out to a maximum temperature of 42° C. for four to five hours, the temperature being controlled within the boundaries of the largest neoplasms, When the temperature reaches 43° to 43.5° C., the temperature is maintained at this level for 1.5 to three hours.

In order to intensify the process of introduction of ferromagnetic particles into cancer cells, it is preferred that a three-dimensional scanning of the whole body with a magnetic field of an intensity of at least 6,000 Oe for five to twenty seconds be carried out before the exposure of the body to the electromagnetic field.

The ferromagnetic particles may be introduced by placing them into capsules having a soluble envelope containing medicinal substances prescribable for a given type of neoplasm.

The above objects are also accomplished by the use of an apparatus for carrying out the method for treating malignant tumors by local hyperpyrexia, comprising a common base supporting a power supply having an output to which is connected a controlled source of electromagnetic radiation having outputs connected to emitters which are attached to the source by means of flexible holders, temperature pickups connected, via an amplifier unit, to one input of a comparator, a temperature setter connected to a second input of the comparator, and a temperature control unit having an input connected to an output of the comparator and an output connected to a control input of the electromagnetic radiation source. According to the invention, the apparatus is provided with a magnetic retainer mounted on a flexible support and with device for removing the contents of a neoplasm having a hollow perforated needle made of a magnetically soft material, a source of a pulsed magnetic field, a collector, and a vacuum source, the needle being magnetically coupled to the source of a pulsed magnetic field connected to the power supply, and the interior space of the needle communicating with the interior of the collector which communicates with the vacuum source.

It is preferred that the apparatus be provided with a device for transferring ferromagnetic particles through a patient's body to a neoplasm, which comprises a plurality of series-connected electro-magnets connected to a stepping switch, each electro-magnet having a surface engageable with the surface of a patient's body, the position of this surface being adjustable with respect to similar surfaces of adjacent electromagnets, each electromagnet having a through passage having one end terminating in said surface and the other end connected to a pipeline which is connected to the vacuum source.

In case of treating of a mammary gland tumor, it is preferred that the electromagnetic emitter be in the form of a cup-shaped frame which is externally provided with an electrically insulated conductor, the conductor being helically wound between the vertex and base of the frame.

The conductor may be in the form of a tube having its ends communicating with a coolant circulation system for Joule heat removal when such heat is released by the conductor.

A method for treating malignant tumors according to the invention allows local heating of tissues to be carried out within the boundaries of neoplasms and metastases to a strictly preset temperature which is higher than that of the normal surrounding tissue. This result can be achieved in treating malignant tumors in any part of a human body, including neoplasms of deeply seated internal organs.

The apparatus for carrying out the method for treating malignant tumors according to the invention is reliable in operation and easy to handle.

BRIEF DESCRIPTION OF THE DRAWINGS

The invention will now be described with reference to specific embodiments illustrated in the accompanying drawings, in which.

DETAILED DESCRIPTION OF THE INVENTION

Figure 1:
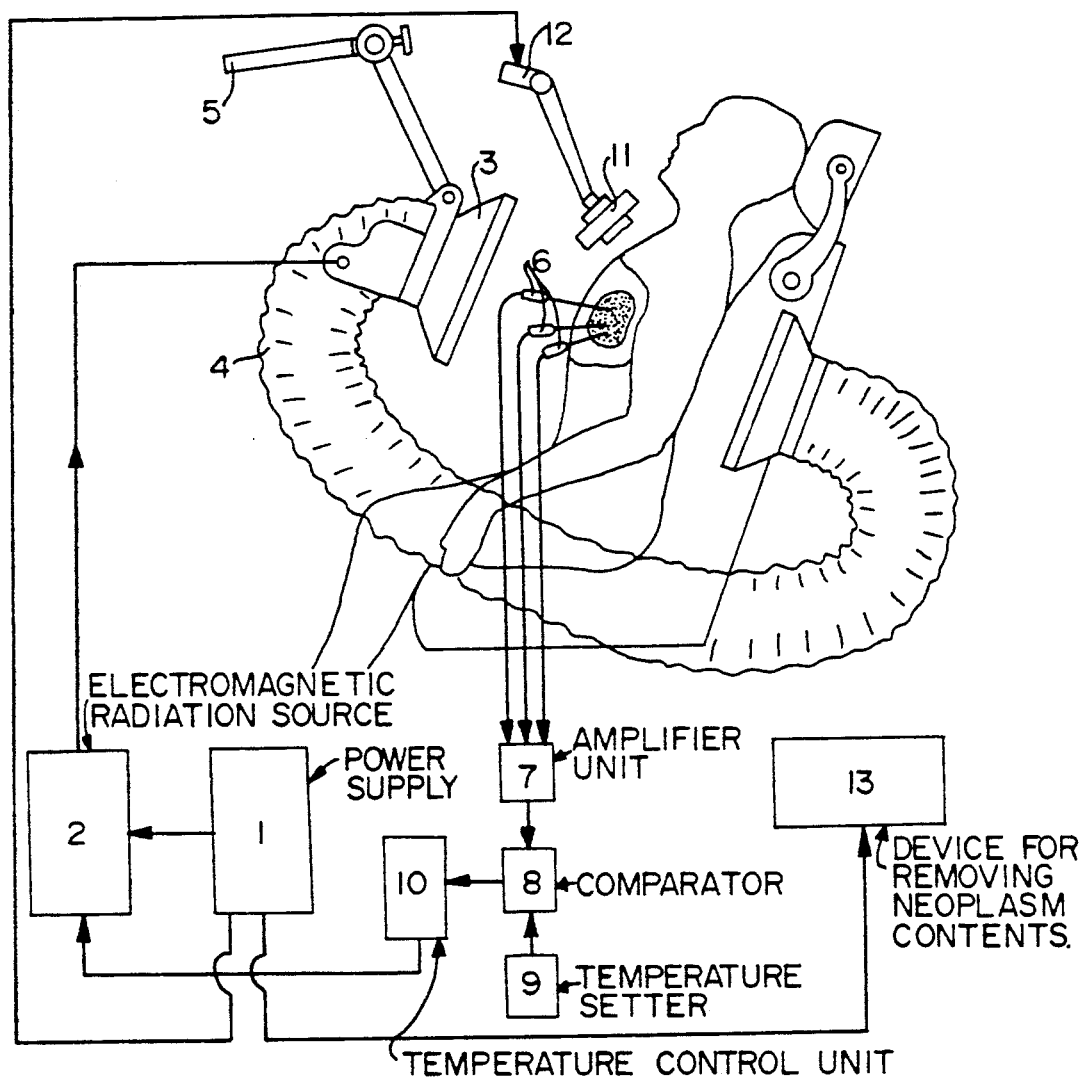
FIG. 1 is a structural diagram of an apparatus for carrying out a method for treating malignant tumors by local hyperpyrexia according to the invention, which schematically shows a patient's body during a local hyperpyrexia treatment.

A method for treating malignant tumors according to the invention resides in the following.

Location and dimensions of a neoplasms are determined in a conventional manner. A suspension containing ferromagnetic particles of a size from $5 \times 10^{-3}$ to $30 \times 10^3$ μm is then introduced into a patient's body in an amount of 0.01 to 0.5 g per each cu. cm of the neoplasm, and movement of the ferromagnetic particles in the body is controlled by X-ray monitoring. After the penetration of the ferromagnetic particles in the neoplasm and their approach to the neoplasm boundary, the patient's body is simultaneously exposed to an electromagnetic field at a frequency of, e.g., 13.65 MHz and power of 200W to carry out hyperpyrexia, and to a magnetic field of, e.g., 6,000 Oe applied to the area of the neoplasm so as to retain the ferromagnetic particles within the boundaries of the neoplasm. The hyperpyrexia is carried out at a temperature sufficient to kill cancer cells, e.g. at 43.5° C. for 90 minutes. After the hyperpyrexia, the neoplasm is removed with ultrasonic oscillations at a frequency from 22 to 100 kHz and intensity from 4 to 100W per 1 sq. cm oft he neoplasm with an exposure time from 0.1 to 5 minutes, and the contents of the neoplasm are then removed. During the treatment, condition of the patient's body is monitored by determining activity of neutrophils and macrophages.

The patient's condition is monitored in the following manner.

Before the introduction of a suspension with ferromagnetic particles into the body, activity of neutrophils and macrophages is determined and, if activity is below 100 bacteria per 100 neutrophils, tafcyn is administered intravenously in a dose of 0.01 to 20 mg per 1 kg of patient's weight. A suspension with ferromagnetic particles is then introduced, and hyperpyrexia is carried out by exposure to the electromagnetic field. Activity of neutrophils and macrophages is again determined and, if activity is below 100 bacteria per 100 neutrophils, tafcyn is again administered, the suspension with ferromagnetic particles is introduced, and hyperpyrexia is repeated. If activity is greater than 100 bacteria per 100 neutrophils, the neoplasm is exposed to ultrasonic oscillations and, after the removal of the neoplasm contents, activity of neutrophils and macrophages is again determined. If the activity is greater than 100, the treatment is stopped, and if the activity is less than 100 bacteria per 100 neutrophils, the treatment is fully repeated.

Activity of neutrophils and macrophages is determined by placing patient's blood in a medium containing (in percent):

| Twin-80 | 0.005–0.05 |
|---|---|
| E. coli | 7–12 |
| Neutrophils | 42–47 |
| Culture medium No. 199 | 42–47 |

Neutrophils are taken by pipet in 2–4 minutes, transferred into a silicone crater of a slide, and bacteria are added at a rate of 10 bacteria per 1 neutophil. Thirty minutes after that, the content of the crater is dyed with an orange dye, and the number of engaged bacteria per 100 neutrophils is counted in a luminescent microscope. With an activity below 100 bacteria per 100 neutrophils, tafcyn in intravenously administered to the body in a dose of 0.01 to 20 mg per 1 kg of patient's weight.

Suspension with ferromagnetic particles may have the following composition (in percent):

| ATP | 1–5 |
|---|---|
| Vitamin C | 10–15 |
| Vitamin B$_6$ | 5–10 |
| Physiologic salt solution | 40 |
| Ferromagnetic particles | the balance |

Depending on location of a neoplasm, the suspension with ferromagnetic particles is administered intravascularly or intrahumoraly, or it is applied topically.

For the case of treatment of neoplasms in the area of mascular tissue, a suspension containing ferromagnetic particles of a size from 1 to 30,000 μm is used which is introduced directly into the neoplasm intrahumoraly.

In case of treatment of neoplasms in internal organs and metastases, a suspension containing ferromagnetic particles of a size from $5 \times 10^{-3}$ to 1 um is used which is administered intravascularly, the ferromagnetic particles being transferred to the neoplasm by a magnetic field.

The embodiment of the method of treatment in case of multiple metastases and malignant tumors resides in the fact that a suspension with ferromagnetic particles is introduced into a vascular bed and locally into large-size neoplasms, with the exposure of the whole body, with the exception of the head, to the electromagnetic field, and the general hyperpyrexia of the body is carried out to a temperature of maximum 42° C. for four to five hours, the temperature being controlled within the boundaries of the largest neoplasms. When the temperature is 43° to 43.5° C., it is maintained there at this level for 1.5 to 3 hours.

In this case, for a more intensive intrusion of particles into cancer cells, a three-dimensional scanning of the whole body with a magnetic field of an intensity of at least 6,000 Oe for 5 to 20 seconds is carried out after the introduction of the suspension and before the exposure to the electromagnetic field.

In addition, metal needle electrodes are inserted into deeply seated neoplasms and into very thick neoplasms before the exposure to the electromagnetic field, the needles being uniformly distributed over the entire surface area of the neoplasms and through the entire thickness thereof. In this case the exposure to the field is effected through the intermediary of electromagnetic coils inductively coupled to each other, one coil being connected to the electromagnetic radiation source, and the other coil, to the electrodes. This facility allows the energy of the high-frequency electromagnetic field to be uniformly distributed over the whole volume of the neoplasm, and uniform heating over the whole volume of the tumor can be achieved with a lower power input of the electromagnetic field.

With the intravascular introduction of suspension, the use is made of ferromagnetic particles placed in capsules having a soluble envelope containing medicinal substances which are prescribable in treating a given type of neoplasm. The soluble envelope of ferromagnetic particles introduced in capsules may contain (in percent by weight of ferromagnetic particles), e.g.:

| Nylon | 8–12 |
|---|---|
| Gelatin | 1–5 |
| Oleic acid | 10–30 |

Concentration, and retainment of ferromagnetic particles, within the boundaries of malignant tumors and metastases under the action of magnetic field allow a local hyperpyrexia to be carried out under the action of electromagnetic field at a temperature which is high enough for killing cancer cells, namely, at points where such particles are located, and traumatism of the surrounding normal tissues is ruled out. The use of a suspension containing ferromagnetic particles of a size smaller than $5 \times 10^{-3}$ μm is inexpedient since a high-power electromagnetic field is necessary to achieve a critical temperature (43.5° C.) so as to result in burns of tissues. In addition, magnetic properties of particles smaller than $5 \times 10^{-3}$ μm are substantially lower so that it would become very difficult to retain them within the boundaries of neoplasm by using a magnetic retainer.

The use of ferromagnetic particles of a size larger than 30,000 μm is also expedient because normal vascular-mascular tissue can be injured by ferromagnetic particles during their movement through a patient's body. A dose of administration of 0.01 to 0.5 g of ferromagnetic particles per 1 cu. cm of a neoplasm was determined by way of experiments.

In carrying out the method of treatment according to the invention, new information is collected about the body, namely, information on activity of neutrophils which characterizes protective capacity of the body, degree and rate of decomposition and removal of the contents of a neoplasm from the body. There is also a possibility of a directional local and concentrated exposure of a neoplasm to the electromagnetic field owing to the use of a suspension containing ferromagnetic particles which is introduced into the neoplasm, with a controlled heating of ferromagnetic particles with this electromagnetic field.

The treatment conducted by using this method allows treatment time to be reduced and traumatism to be lowered, with the control of completeness and rate of removal of the contents of a neoplasm from the body, local hyperpyrexia at any depth in the body, rate of activation of protective capacity of the body, which can enhance efficiency of treatment as a whole.

The treatment method according to the invention may be carried out using an apparatus shown in FIGS. 1, 2, 3, 4, 5, 6, 7.

The structural diagram of an apparatus according to the invention, which is shown in FIG. 1, comprises a common base (not shown in the structural diagram) supporting a power supply 1 having an output to which is connected a controlled electromagnetic radiation source 2, e.g., a variable high-frequency generator having an output to which are connected flat emitters 3 electrically coupled to each other by means of a solenoid 4. One emitter 3 is mechanically coupled to the base by means of a flexible holder 5, and the other emitter is incorporated in a patient's seat structure. The apparatus also has temperature pickups 6 connected, via an amplifier unit 7, to a first input of a comparator 8, a temperature setter 9 connected to a second input of comparator 8, and a temperature control unit 10 such as an attenuator having an input connected to an output of comparator 8 and an output connected to a control input of electromagnetic radiation source 2. The apparatus also has a magnetic retainer 11 such as an electromagnet connected to an output of power supply 1 and attached to the base by means of a flexible holder 12, and a device 13 for removing a neoplasm mounted on the same base.

Figure 2:
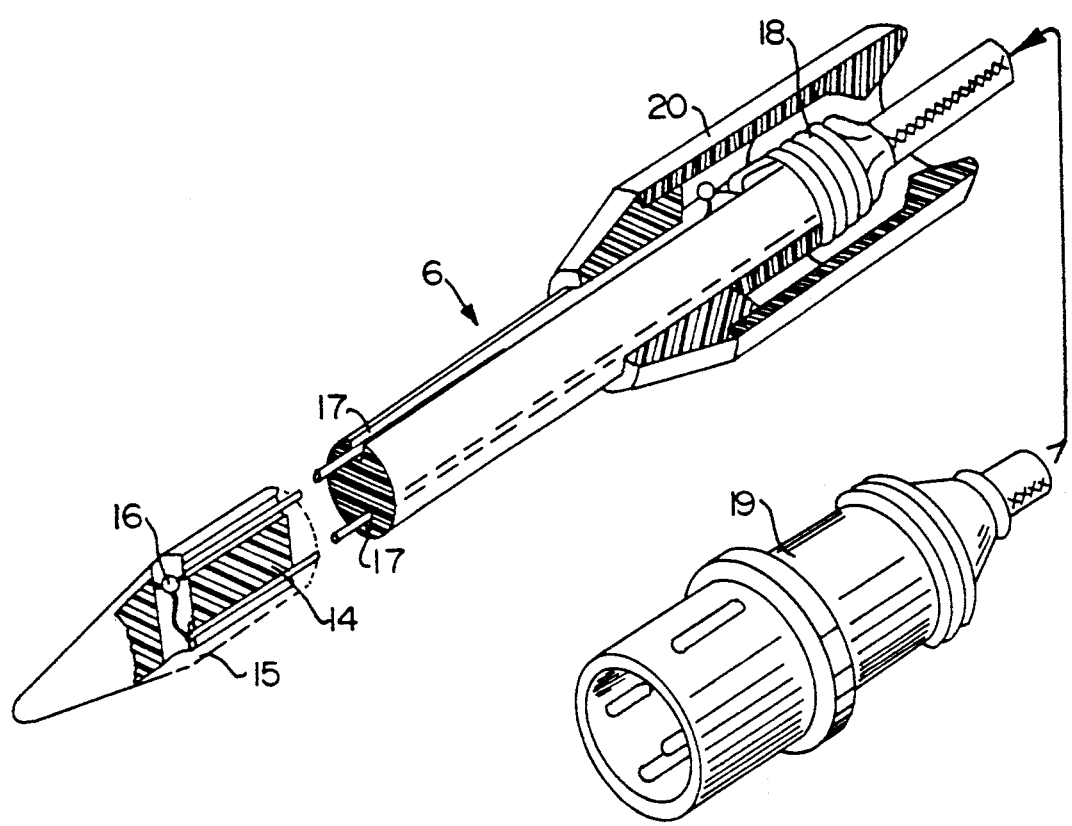
FIG. 2 shows an enlarged perspective view, in section, of a temperature pickup.

The construction of one of temperature pickups 6 is shown in FIG. 2. Temperature pickup 6 is made in the form of a surgical needle 14, 1.0 to 2.0 mm in diameter and 50 to 200 mm long made of a biologically neutral material, e.g., of polyamide. A transverse through hole 15 is made adjacent to the point of needle 14, and a thermoresistor 16 in the form of a sensor is incorporated in this hole. Leads of thermoresistor 16 are located in two diametrically opposed longitudinal passages 17 of needle 14. The leads of thermoresistor 16 are connected, adjacent to the blunt end of needle 14, to a cable 18 having a jack 19 at the other end for connecting to a plug of amplifier unit 7 (FIG. 1). The zone of connection between leads of thermoresistor 16 and cable 18 is protected with an insulating guard sleeve 20 which also functions as a handle of pickup 6.

Figure 3:
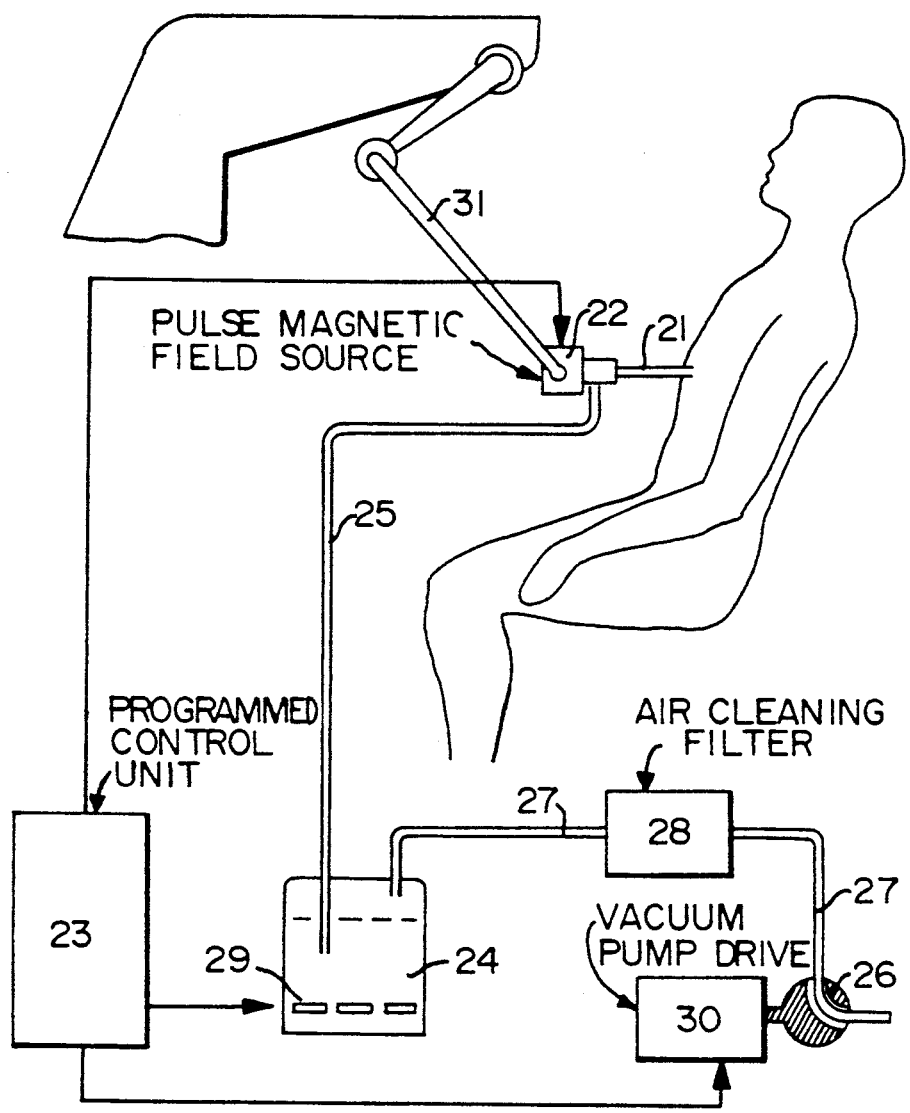
FIG. 3 is a structural diagram of a device for removing the contents of a neoplasm which schematically shows a patient during the removal of the contents of a neoplasm.
Figure 4:
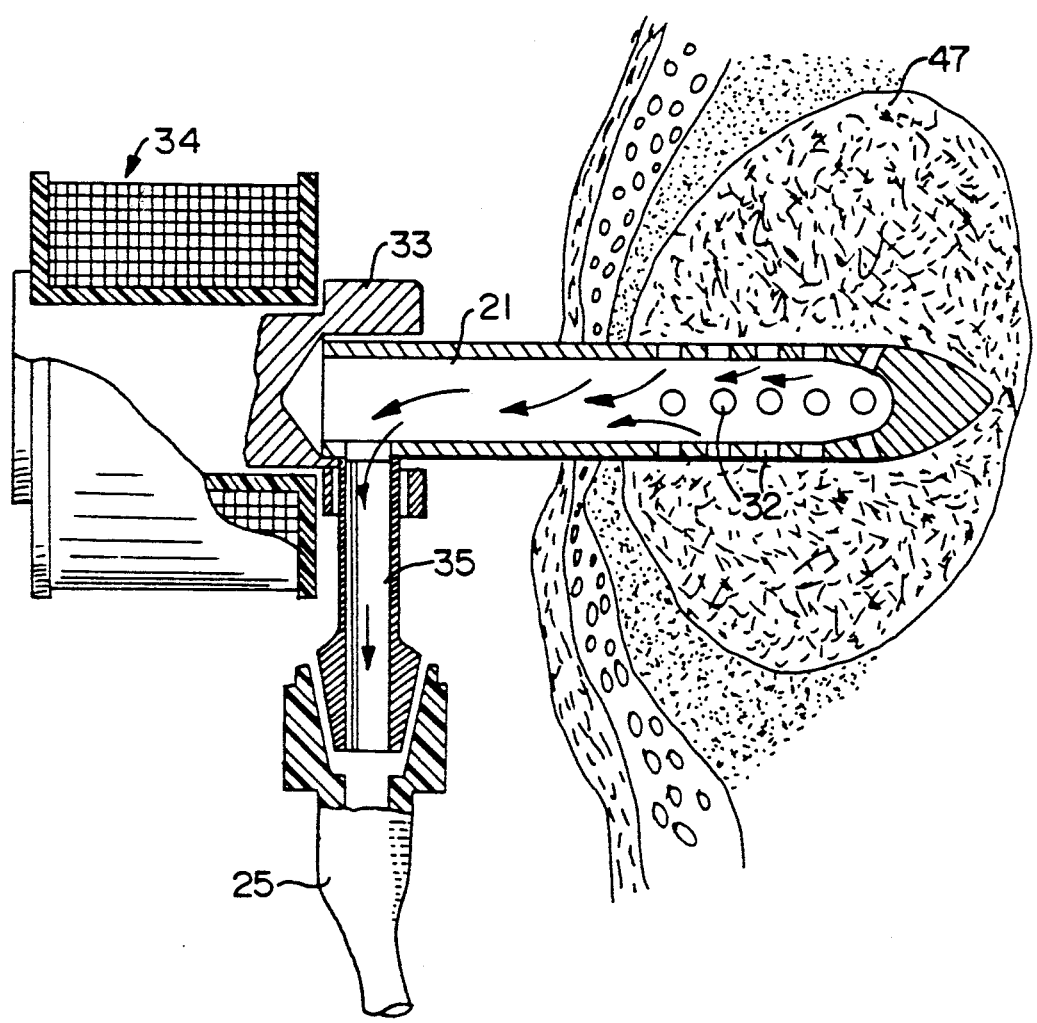
FIG. 4 shown an enlarged view, in section, of a magnetic needle having a source of magnetic field, which is introduced into a neoplasm.
Figure 5:
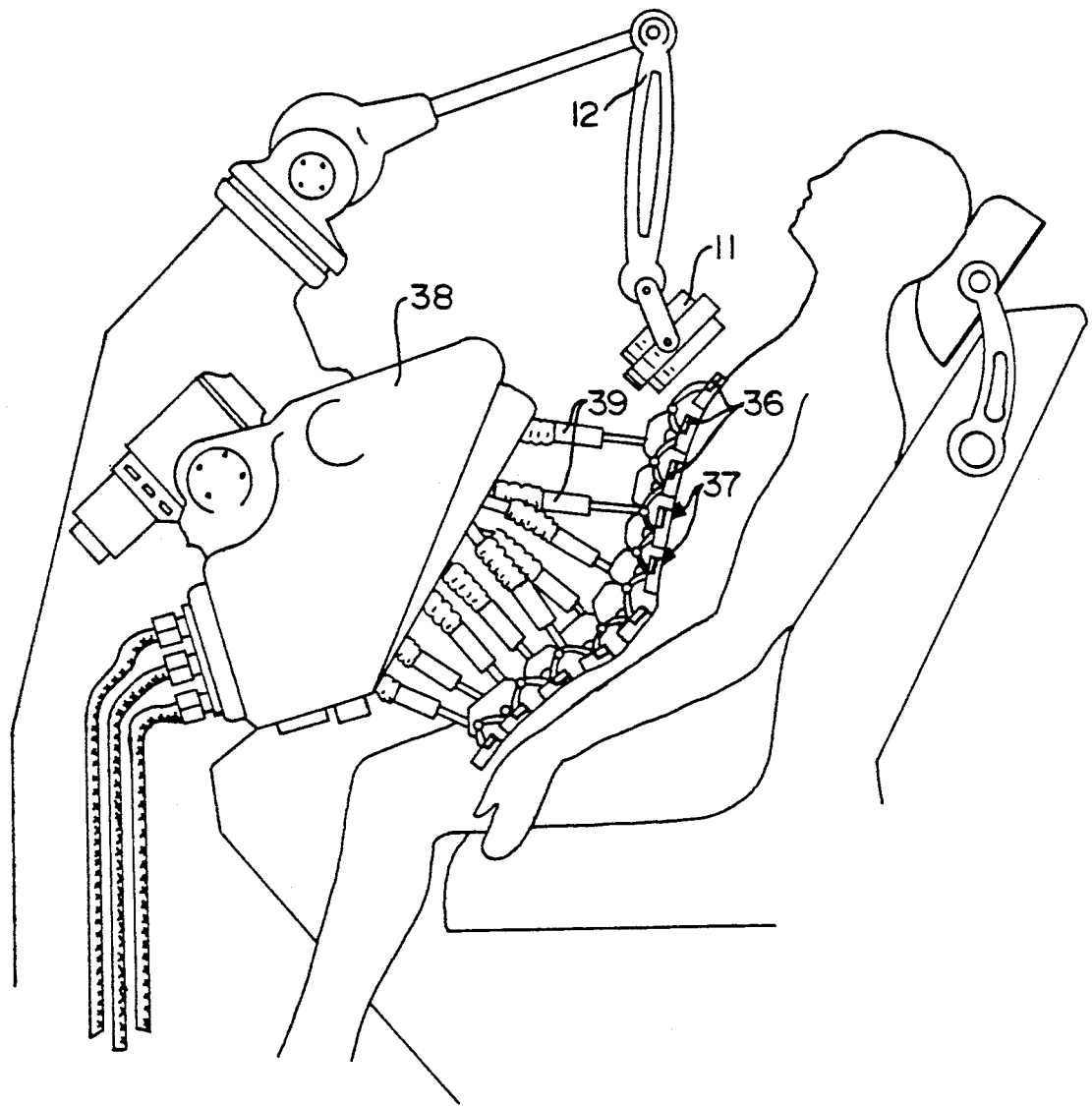
FIG. 5 is a general view of a device for transferring ferromagnetic particles and a magnetic retainer, with a schematic representation of a patient during the transfer of ferromagnetic particles to a neoplasm.

The device for removing the neoplasm contents shown in FIGS. 3 and 4 comprises a hollow needle 21 (FIG. 3) magnetically coupled to a source 22 of pulsed magnetic field connected to a programmed control unit, a collector 24 communicating, via a pipeline 25, with the interior space of needle 21, and a vacuum source 26, e.g., a vacuum pump in this embodiment, connected by means of a pipeline 27, via an air cleaning filter 28, with the interior space of collector 24. The latter is provided with an electrostatic screen 29 which enhances the effect of separation of mechanical metal impurities. Programmed control unit 23 is also electrically coupled to electrostatic screen 29 and to a drive 30 of the vacuum pump. Hollow needle 21 is secured in a flexible holder 31.

Needle 21 has, at its pointed end, perforations 32 (FIG. 4) of a size corresponding to the size of ferromagnetic particles, the other end of the needle being incorporated in a core 33 of an electromagnet 34 which functions as a source of pulsed electromagnetic field. Needle 21 is made of a magnetically soft material. The interior space of needle 21 communicates with pipeline 25 by means of a socket pipe 35.

The device for transferring ferromagnetic particles through a patient's body between the point of injection and a neoplasm comprises a plurality of series-connected electromagnets 36 connected to a stepping switch. The stepping switch may be built around, e.g., thyristors, the number of thyristors being equal to the number of electromagnets, the thyristors having different firing thresholds. The thyristors are connected in series so as to ensure a stepwise increase in their firing threshold. As such stepping switch is widely known, it is not shown in FIG. 5.

Each electromagnet 36 has a surface 37 engageable with a patient's body, and position of this surface is adjustable with respect to position of similar surfaces 37 of adjacent electromagnets 36. This construction allows a magnetic tract to be provided on any surface of a human body to follow the relief of the body.

Electromagnets 36 are pressed against a patient's body by means of an electropneumatic manipulator 38 electrically coupled to power supply 1 (FIG. 1) and pneumatically connected to vacuum source 26 (FIG. 3). Each electromagnet 36 (FIG. 5) has a through passage having one end terminating in surface 37 and the other end communicating, via a pipe 39, with the pneumatic system of manipulator 38.

Figure 6:
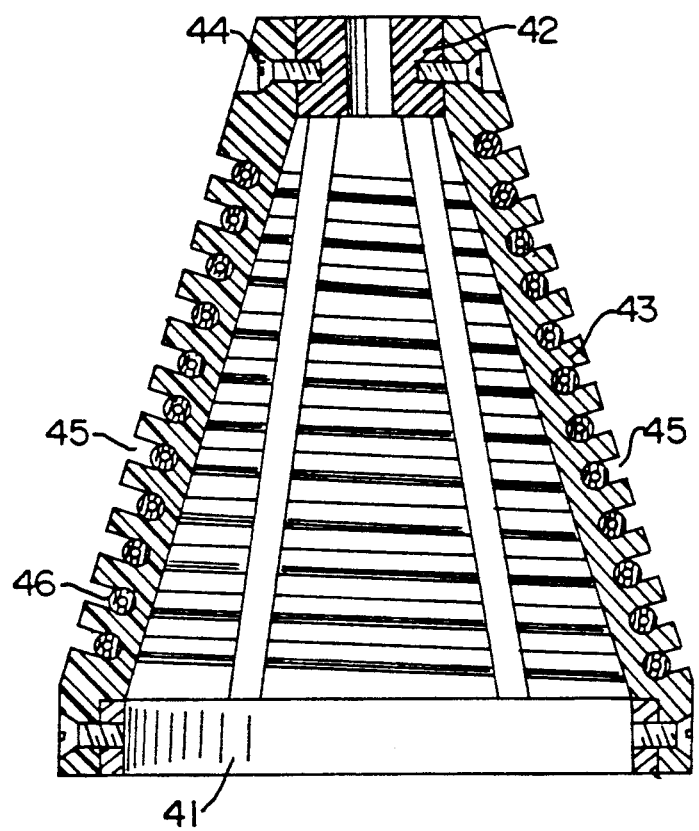
FIG. 6 is a sectional view of an electromagnetic emitter shown for the case of a neoplasm of the mammary gland, according to the invention.
Figure 7:
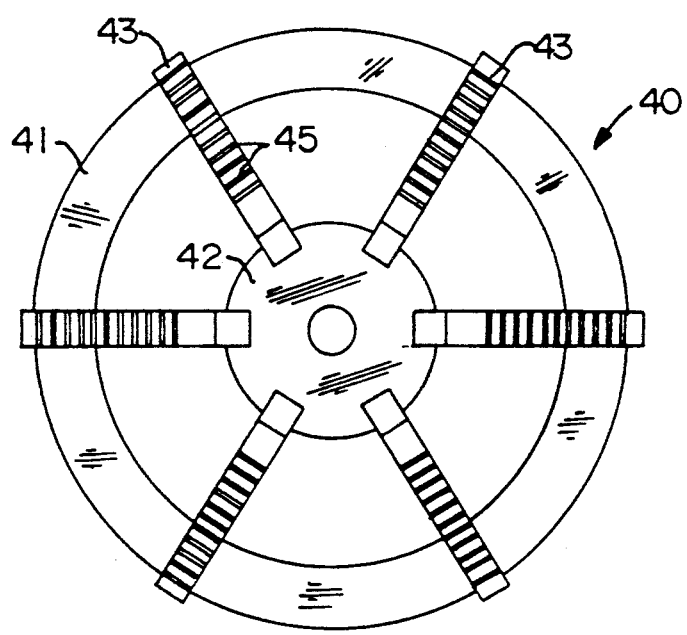
FIG. 7 is a top view of a frame of the emitter shown in FIG. 6.

The embodiment of an electromagnetic radiation emitter shown in FIGS. 6 and 7 for the case of treatment of a neoplasm of the mammary gland has a rigid cup-shaped frame 40 made of a heat insulating material. Frame 40 consists of a lower base 41 in the form of a ring and has a ring-shaped upper base 42 of a smaller diameter, and ridges 43 secured by screws 44 to upper and lower bases 41 and 42. Ridges 43 have transverse snap grooves 45 which narrow down, and an electrically insulated conductor 46 is placed in these grooves which is helically wound between upper base 41 and lower base 42 of frame 40. Terminations are provided at the ends of conductor 46 for connecting to a high-frequency generator (not shown in FIGS. 6, 7). In this embodiment, conductor 46 is in the form of a copper tube which is internally and externally provided with an electrically insulating lining, the interior space of the tube communicating with a coolant circulation system (not shown in FIGS. 6 and 7).

The emitter shown in FIGS. 6 and 7 is used for local hyperpyrexia of the mammary gland which is placed directly inside the emitter. This allows the electromagnetic radiation to be concentrated directly in the tumor.

The apparatus shown in FIGS. 1 through 5 is used in the following manner.

Temperature pickups 6 are introduced into the body of a patient to a desired depth through a puncture in live tissue made in advance by a metal needle which is used for the introduction of a suspension with ferromagnetic particles into the area of a malignant tumor.

The provision of parts of temperature pickup 6 made of nonmetals rules out temperature measurement errors under the action of high-frequency radiation and ensures accuracy of absolute temperature readings of about 0.05° C. At the same time, the nonmetal structure has a low heat capacity so as to avoid inertia of transient temperature gradients.

This is a very important for control signals of an automatic power control circuit of a high-frequency generator to maintain a preset temperature from 42° to 43° C. in the area of a neoplasm in which suspension with ferromagnetic particles is introduced.

Ferromagnetic particles introduced into the area of a neoplasm and fragments of tumoral tissue to be removed are removed by means of device 13 (FIG. 1) for removal of contents of a neoplasm.

Perforated hollow needle 21 (FIG. 4) is introduced, with its pointed end, after the completion of hyperpyrexia and ultrasonic irradiation, into the area of a malignant tumor 47. D-c pulses are supplied to the coil of electromagnetic 34 from power supply at regular intervals (every 5 to 10 seconds) in response to signals fed from the output of unit 23, whereby needle 21 is magnetized and demagnetized at the same time intervals. During periods of magnetization of needle 21, ferromagnetic particles are entrained under the action of magnetic forces into perforations 32, and these particles are then admitted from the interior space of needle 21, through pipeline 25, to collector 24 to be attracted there by electrostatic screen 29. During periods of demagnetization of needle 21, contents of the tumor are sucked in the interior space of needle 21 through perforations 32 owing to a pressure differential provided by vacuum source 26, and this material is also transferred through pipeline 25 into collector 24.

The method for treating malignant tumors according to the invention by using the apparatus according to the invention was tested in animals.

EXAMPLE 1

A rat of 250 g was taken, and a tumor of Walker sarcoma was grafter to the femur muscles. The tumor has grown to 2.5 cu. cm by the seventh day. A suspension containing ferromagnetic particles of a size from $5 \times 10^{-3}$ to 50 μm was introduced in a dose of 2 cu. cm at the seventh day, and 2 cu. cm of a suspension with ferromagnetic particles of a size of $5 \times 10^{-3}$ μm was introduced into lymphatic vessels and blood bed. The suspension was moved by a magnetic field towards the tumor. When the suspension particles got into the tumor and reached the tumor boundaries, a local hyperpyrexia was carried out by exposing the neoplasm to electromagnetic waves at 13.65 MHz with a power of 100W during one hour to a temperature of 43° C. in the neoplasm which was controlled by single temperature pickup 6. Three hours after the beginning of the test, immunocompetent status of the body in response to the treatment was determined. The number of neutrophils changed from 100 to 125.

Twelve hours after the beginning of the test, the tumor was exposed to ultrasonic oscillations at 25 kHz with a power of 10W per sq. cm for five minutes, and the contents of the tumor were then removed by device 13 for removal of the contents of a neoplasm with metal particles, which worked in the pulse mode in 3-second periods for 15 minutes. As a result of the test, tumor could not be detected in the body in twelve days.

The method of treatment according to the invention with the use of the apparatus according to the invention was used for treating a group of oncologic patients, and positive results were achieved.

EXAMPLE 2

Female patient T. of 42 was admitted to a clinic with rhabdomyosarcoma of soft tissues of the right femure of a size of 350 cu. cm. Activity of neutrophils and macrophages was below 100. A suspension (3 g) containing ferromagnetic particles of a size of 1 to 25 μm in 9 cu. cm. of gelatin was introduced directly into the tumor. The introduction of the suspension was X-ray controlled.

When the ferromagnetic particles reached the boundaries of the tumor, the tumor was locally exposed to a permanent magnetic field of 6,000 Oe to retain the particles within the tumor boundaries. At the same time, the tumor was exposed to an alternating electromagnetic field at a frequency of 13.65 MHz to carry out a local hyperpyrexia during 120 minutes. Temperature within the tumor boundaries was maintained at the level of 43.5° C. The temperature was measured by means of two temperature pickups 6 and controlled by varying intensity of electromagnetic field. After the 120-minute exposure, the electromagnetic field was removed, and the tumor was exposed to ultrasonic oscillations at 25 kHz, with an intensity of 2W per sq. cm of the tumor surface during one minute, and the ultrasonic action was then stopped. In 24 hours after the treatment, the softened contents of the neoplasm with ferromagnetic particles were removed. Forty days after the beginning of the treatment, patient T. was examined morphologically to study changes in the tumor. The examination showed that no tumor elements were revealed in the studied portions of the skin, subcutaneous fat, and muscular tissued. The tumor has disappeared. Activity of neutrophils increased to 120. Patient T. was discharged 20 days after the beginning of the treatment.

EXAMPLE 3

Female patient R. of 52 was admitted to a clinic with synovial sarcoma of the foot of a size of 150 cu. cm after relapses following a repeated surgical treatment. Activity of neutrophils was below 100. A suspension (2 g) containing ferromagnetic particles of a size of 1 to 25 μm was introduced directly into the tumor in 6 cu. cm of gelatin. The introduction of the suspension was checked with the aid of X-ray monitoring. When the ferromagnetic particles reached the boundaries of the tumor, the tumor was locally exposed to a permanent magnetic field of 6,000 Oe and simultaneously to an alternating electromagnetic field at 13.65 MHz to carry out local hyperpyrexia for a period of 120 minutes. Temperature of 43.5° C. was maintained. The treatment was then carried out as described in Example 2.

Morphological examination of patient R. was then carried out 1.5 months after the beginning of the treatment. The examination showed that no tumor elements were revealed, and activity of neutrophils increased to 110.

Patient R. was discharged one month after the beginning of the treatment.

EXAMPLE 4

Female patient P. of 35 was admitted to an oncologic outpatient clinic with the cancer of the mammary gland. A tumor was maximum 3 cm in the largest dimension. Puncture biopsy showed the presence of cells of adenocarcinoma. Activity of neutrophils was below 100. A suspension with ferromagnetic particles was introduced into the patient intrahumoraly and into the tissues surrounding the tumor. The dimensions of the contrast portion of the mammary gland defined by the suspension were 5×6 cm. Seven needle electrodes were introduced into the neoplasm through the whole depth of the tumor of 5 cm, and the needles were uniformly distributed. A local hyperpyrexia was then carried out by exposing to an electromagnetic radiation at 13.65 MHz with a power of up to 20W. The helical emitter according to the invention was used. Two days after the hyperpyrexia treatment, a sectoral radical removal of the tumor with the ferromagnetic particles was carried out. Morphological test of the removed sector of the mammary gland with the ferromagnetic particles showed the absence of cancer cells.

We claim:

1. A method for treating a malignant tumor in a patient which comprises the steps of:
   (a) determining the location and dimensions of said tumor in said patient's body;
   (b) determining the activity of neutrophils and macrophages, and if said activity is below 100 bacteria per 100 neutrophils, administering tuftsin intravenously to said patient in a dose of 0.01 to 20 mg per 1 kg of patient's body weight;
   (c) introducing into said patient's body a suspension containing ferromagnetic particles having a size of from $5 \times 10^{-3}$ to $30 \times 10^3$ $\mu$m, and in an amount of from 0.01 to 0.05 g per each cu. cm of said tumor;
   (d) monitoring the movement of said ferromagnetic particles through said patient's body by x-ray, and determining the time that said particles penetrate and approach the boundaries of said tumor;
   (e) at that time exposing said patient's body to an electromagnetic field at an intensity and for a period of time sufficient to cause hyperpyrexia within said tumor and at a temperature of from 43° to 43.5° C. to ensure destruction of cancer cells in said tumor;
   (f) simultaneously with the exposure to said electromagnetic field, exposing said tumor to a magnetic field of an intensity sufficient to retain ferromagnetic particles in said tumor;
   (g) determining the activity of neutrophils and macrophages and if said activity is below 100 bacteria per 100 neutrophils repeating steps (b)-(f);
   (h) when said activity is greater than 100 bacteria per 100 neutrophils, exposing said tumor to ultrasonic oscillations with said subsequent removal of the contents of the tumor; and
   (i) again determining the activity of neutrophils and macrophages and if said activity is below 100 bacteria per 100 neutrophils repeating steps (b)-(f).

2. The treatment method according to claim 1, when said treatment of said tumor is carried out in muscular tissue, wherein said suspension contains said ferromagnetic particles of a size 1 $\mu$m to 30,000 $\mu$m and is introduced directly into said tumor.

3. The treatment method according to claim 2, wherein, before said exposure to said electromagnetic field, metal needle electrodes are introduced into said tumor to ensure their uniform distribution over the surface area of said tumor and through the entire thickness of said tumor.

4. The treatment method according to claim 1, when said treatment of said tumor is carried out in internal organs and metastases, wherein said suspension contains said ferromagnetic particles of a size of $5 \times 10^{-3}$ to 1 $\mu$m and is administered intravascularly so as to ensure the transfer of said ferromagnetic particles to said tumor by said magnetic field.

5. The treatment method according to claim 1, when said treatment is carried out in multiple metastases and malignant tumors of various internal organs and soft tissues, wherein said suspension is introduced into a vascular bed and locally into the largest tumors; the whole body being exposed to said electromagnetic field, with the exception of the head, general hyperpyrexia of said body being carried out initially at a temperature of maximum 42° C. for 4 to 5 hours; controlling the said temperature within the boundaries of said largest tumors and, when temperature has reached locally 43° to 43.5° C. within said boundaries, maintaining the temperature at this level for 1.5 to 3 hours.

6. The treatment method according to claim 5, wherein, after said introduction of said suspension and before said exposure of said body to said electromagnetic field, a three-dimensional scanning of a whole body with a magnetic field with an intensity of at least 6,000 Oe is carried out during 5 to 20 seconds.

7. The treatment method according to claim 5, wherein said ferromagnetic particles are introduced in capsules having a soluble envelope containing medicinal substances which are prescribable for a given type of tumor.

8. In a method for treating malignant tumors, comprising determining location and dimensions of a malignant tumor in a patient's body; introducing into said patient's body a suspension containing ferromagnetic particles of a size ranging from $5 \times 10^{-3}$ to $30 \times 10^3$ m in an amount of 0.01 to 0.5 g per 1 cm$^3$ of said tumor; carrying out x-ray monitoring of movement of said ferromagnetic particles within said patient's body after said introduction; determining, in carrying out said x-ray monitoring, a moment at which said particles penetrate said tumor and a moment at which said particles has reached boundaries if said tumor as a result of propagation of said particles through the whole volume of said tumor; exposing said patient's body, beginning with said movement at which said particles has reached the tumor boundaries, to an electromagnetic field with a frequency, power and exposure time which are capable of ensuring a local hyperpyrexia within said boundaries of said tumor at a temperature ranging from 43° to 43.5° C. ensuring destruction of cancerous cells; monitoring condition of said patient's body during said treatment by checking up the level of activity of neutrophils and macrophages, the improvement which comprises simultaneously with said exposure to an electromagnetic field, exposing said malignant tumor to a magnetic field having an intensity ensuring retention of said ferromagnetic particles within said boundaries of said tumor.

* * * * *